United States Patent
Uflacker

(10) Patent No.: US 7,803,171 B1
(45) Date of Patent: Sep. 28, 2010

(54) RETRIEVABLE INFERIOR VENA CAVA FILTER

(76) Inventor: Renan P. Uflacker, 548 Overseer's Retreat, Mt. Pleasant, SC (US) 29464

( * ) Notice: Subject to any disclaimer, the term of this patent is extended or adjusted under 35 U.S.C. 154(b) by 1303 days.

(21) Appl. No.: 10/866,886

(22) Filed: Jun. 14, 2004

(51) Int. Cl.
*A61M 29/00* (2006.01)

(52) U.S. Cl. .................................................... 606/200

(58) Field of Classification Search ............... 606/159, 606/194, 198, 200
See application file for complete search history.

(56) References Cited

U.S. PATENT DOCUMENTS

| | | | | |
|---|---|---|---|---|
| 5,626,605 | A * | 5/1997 | Irie et al. ....................... | 623/1.1 |
| 5,746,767 | A * | 5/1998 | Smith ........................... | 606/200 |
| 5,853,420 | A * | 12/1998 | Chevillon et al. ............ | 606/200 |
| 6,007,558 | A * | 12/1999 | Ravenscroft et al. ........ | 606/200 |
| 6,231,589 | B1 * | 5/2001 | Wessman et al. ............ | 606/200 |
| 6,436,121 | B1 | 8/2002 | Blom | |
| 6,972,025 | B2 * | 12/2005 | WasDyke ..................... | 606/200 |
| 2003/0097145 | A1 * | 5/2003 | Goldberg et al. ............ | 606/200 |
| 2003/0208227 | A1 * | 11/2003 | Thomas ........................ | 606/200 |
| 2004/0059373 | A1 * | 3/2004 | Shapiro et al. .............. | 606/200 |
| 2004/0088001 | A1 * | 5/2004 | Bosma et al. ................ | 606/200 |
| 2004/0116959 | A1 * | 6/2004 | McGuckin et al. .......... | 606/200 |
| 2004/0193209 | A1 * | 9/2004 | Pavcnik et al. .............. | 606/200 |
| 2004/0230220 | A1 * | 11/2004 | Osborne ....................... | 606/200 |

* cited by examiner

*Primary Examiner*—Anhtuan T Nguyen
*Assistant Examiner*—Julie A Szpira
(74) *Attorney, Agent, or Firm*—Damon Morey LLP

(57) ABSTRACT

The present invention provides an intravascular filter for minimally invasive deployment into, and extraction from, a blood vessel. The invention comprises an inferior vena cava filter used to prevent migration of clots into the pulmonary artery wherein the filter has a novel architecture such that the filter can be extracted from the vessel without substantially damaging the vessel, even after prolonged periods of deployment.

8 Claims, 4 Drawing Sheets

RETRIEVABLE INFERIOR VENA CAVA FILTER

FIELD OF THE INVENTION

The present invention relates generally to implantable blood filters. More particularly, the invention relates to implantable blood filters having features enabling extraction of the filter.

BACKGROUND OF THE INVENTION

Pulmonary embolism, in which emboli from any of various regions of the vascular system pass into the lungs, accounts for thousands of deaths each year in the United States. Pulmonary embolisms typically occur when blood clots from the lower extremities are carried to the heart through the inferior vena cava (IVC), and from there to the pulmonary arteries within the lungs.

Many patients with documented pulmonary embolism (PE) can be treated with anti-coagulants to prevent further formation of thrombi, but there are situations in which mechanical interruption of the inferior vena cava is the preferred method to prevent pulmonary embolism. To prevent blood clots from passing upwardly through the inferior vena cava, filters have been placed in the vessel to trap potentially dangerous blood clots.

Conventional implantable blood filters employing a variety of geometries are known. Many are generally basket or cone shaped in order to provide adequate clot-trapping area while permitting sufficient blood flow. Also known are filters formed of various loops of wire, including some designed to partially deform the vessel wall in which they are implanted. Vena cava filters commonly include a core portion from which a plurality of wires radiate outwardly. The wires serve to filter clots from blood flowing through the vein. Various hook-like projections, barbs and the like have been suggested for use in holding the filter in place once the delivery catheter has been withdrawn.

Traditional indications for filters are patients with deep venous thrombosis, and with a contraindication for anticoagulation, or patients with large floating clots in the iliac veins or IVC, with an imminent risk of embolism. Additional contraindications are young patients or patients with a transient problem that may cause PE, not requiring a permanent filter. However, one important problem with many available intravascular filters in use is the non-retrievability of the devices, because while penetration of the retaining hooks of the filter into the lumen of the IVC is necessary for the proper anchoring of the device, in extreme cases and over time, overpenetration may impinge upon adjacent organs, leading to serious or even fatal complications. Further, with time the filter will be integrated into the aortic wall, making it unretrievable without causing significant damage to the vessel wall, particularly at the body of the basket. Accordingly, a vena cava filter capable of temporary deployment is desired to provide rapid protection against pulmonary embolism. However, as the condition producing blood clots is successfully treated, it may be desired to remove the filter from the vena cava.

There is therefore a need for a safe and effective intravascular filter that can be left in place permanently or deployed and subsequently removed by minimally invasive techniques and without causing substantial damage to the vessel wall, even after passage of such time that portions of the filter wires become integrated into the aortic wall.

SUMMARY OF THE INVENTION

The present invention meets the above described need by providing an intravascular filter for minimally invasive deployment into, and extraction from, a blood vessel. The invention comprises an inferior vena cava filter used to prevent migration of clots into the pulmonary artery wherein the filter has a novel architecture such that the filter can be extracted from the vessel without substantially damaging the vessel, even after prolonged periods of deployment.

DETAILED DESCRIPTION OF THE INVENTION

Figure 1:
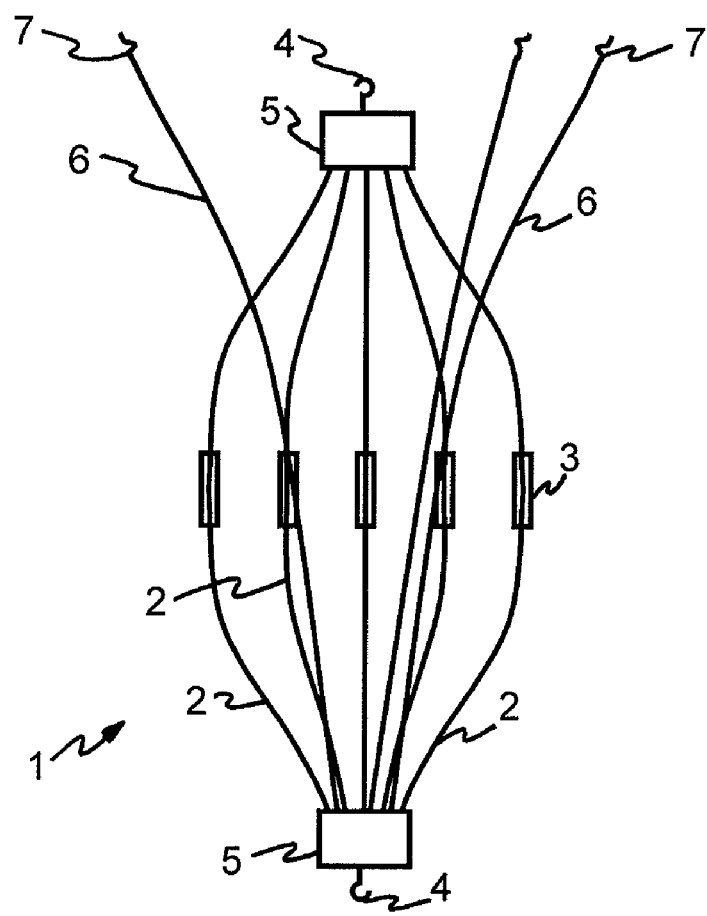
FIG. 1 is a side view of the filter assembly with its first and second portions connected by connecting tubes.

The present invention comprises a filter intended to be inserted into vessels of a living being by a minimally invasive delivery system. Further, the filter provided by the present invention is fully retrievable after the danger of PE has abated, the retrieval does not involve significant surgery, and the design of the filter mitigates damage to the vessel upon retrieval.

Accordingly, in one embodiment of the invention, a filter assembly is provided which includes a first and a second portion. Each portion has a plurality of flexible, resilient wires comprising filtering elements extending distally from a core which forms the apex of the filter assembly. The core further includes an extraction appendage which may be in the form of a hook or loop or similar means for use in the extraction of the filter assembly as described more fully below. The filter assembly may or may not also comprises anchoring wires which include gripping elements. The anchoring wires are connected to and extend distally from at least one core of the filter assembly.

When the filter is initially deployed within a vessel, the filtering elements are detachably interposed within connecting tubes such that the first and second portions of the filter assembly are held together by the distal ends of the filtering elements interposed within the connecting tubes. In one embodiment, the connecting tubes may have fixation elements which prevent further migration of the filter. The distal ends of the filtering elements interposed within the connecting tubes may be held in place, by for example, frictional force between the elements and the tubes, crimping or any suitable means.

The wires employed in both the filter and anchoring wires are flexible and resilient, and are capable of being elastically deformed from a predetermined configuration (as where the wires, unconfined by delivery catheter, are in contact with the walls of the vena cava) to another configuration (as when the wires are elastically confined within the proximal end portions of catheter) and of elastically regaining, at least in part, their predetermined configuration. The wires are preferably formed of a biocompatible material such as stainless steel, cobalt-chromium alloys, titanium, etc. Preferably, the wires of each portion of the filter and anchoring elements are so disposed with respect to each other as to be out of contact with each other distally of their respective apices when the filter assembly is deployed in the lumen of a vessel. Further, because the vena cava and other large vessels of the venous system are thin walled and are easily perforated, in one embodiment, the wires and/or anchoring elements of the filter assembly may terminate in enlarged ends which may be rounded, generally spheroidal, or kinked such that the walls of the vena cava are not perforated by the distal ends during extraction of the first and second portions of the filter assembly, as described more fully below.

The unique characteristics of the filter assembly of the present invention provide physicians, particularly interventional radiologists, with various options for deployment of the filter assembly for either a temporary or permanent placement. Accordingly, the filter is such that it may be delivered by a delivery catheter having an inner bore within which the filter assembly is slidably received. In general, vena cava filters are introduced into the vasculature through a puncture or an incision in a major vessel such as the internal jugular vein or femoral vein. The filter, restrained in a delivery catheter, is passed from the jugular vein through the right atrium of the heart and into the inferior vena cava whereupon the filter is mechanically expelled from the catheter and expands into contact with the vessel lumen. The delivery catheter may be inserted into the vessel until its distal end is positioned adjacent to the desired location for placement of the filter assembly wherein the first and second portions of the filter assembly are connected by the connecting tubes. When the catheter has been appropriately positioned within the vena cava using routine techniques, the filter assembly is slidably moved to the distal end of the delivery catheter and the delivery catheter is removed proximally to free the filter assembly which allows the wires and connecting tubes to contact the lumen of the vessel with the connecting tubes and optionally part of the wires laying in contact against and along the lumen of the vessel for a distance sufficient to substantially center the filter core in the lumen. In this way, the entire filter assembly may be deployed in the lumen by passing it through a properly positioned delivery catheter, using a dilator or other push-rod within the catheter and according to well known techniques.

Unconfined, the anchoring element and filter wires elastically expand radially, the wires converging at the filter core to form the apex of the deployed filter. The anchoring elements, such as proximally facing hooks, prongs or the like, are carried by the anchoring wires. As the latter wires are elastically pressed against the vessel walls, the gripping elements grip the walls to anchor the filter assembly in place. The filter assembly with first and second portions connected by the connecting tubes is thus left behind with the apex centrally disposed within the lumen as the catheter is removed from the body. By "centrally disposed" or "substantially centered" or the like in connection with the position of the apex it is meant that the apex is positioned within about the central one-half, preferably the central one-third, of the diameter of the lumen.

To remove the filter assembly, a removal catheter similar to the delivery catheter may be used wherein the removal catheter has a means, such as a snare, for attaching to the extraction appendage connected to the core of each portion of the filter assembly. The first and second portions of the filter assembly may be removed sequentially or simultaneously, wherein the first and second portions are retrieved into a catheter in opposite directions from each other.

Now, referring first to FIG. 1, a filter assembly of the invention is designated as numeral 1. Generally cylindrical cores 5 are shown from which extend a plurality of circumferentially spaced wires 2, the wires from each core extending distally and outwardly in a generally conical configuration. Near their respective ends distal to the cores, the wires are interposed into connecting tubes 3. The connecting tubes, while presented in the figures as fixed in a plane perpendicular to the longitudinal axis of the filter assembly, may also be present in a staggered configuration. It will therefore be obvious to those skilled in the art that the length of the filter wires will be intimately correlated with the position of the connector tubes. For example, connector tubes in a plane perpendicular to the longitudinal axis of the filter assembly wherein the plane is in the center of the filter assembly will require filter wires of substantially equal length, whereas staggered connector tubes will require different lengths of filter wire extending from opposite cores such that in either case, a pair of filter wires joined by a connecter tube will substantially extend the length of the filter assembly to connection points in the respective cores.

With respect to the figures and for the purpose of the specification and claims herein, a "portion" of the filter assembly, as in "first portion" or "second portion", refers to the set of features which comprises a core 5, an extraction appendage 4, and filter wires 2 up to ends of the filter wires distal to their respective cores 5. Further, at least one of the first or second portions of the filter assembly may further comprise the anchoring wires 6 and the associated anchoring elements 7.

The anchoring wires 6 include at their ends anchoring elements 7. The anchoring elements can be of any type capable of gripping to the walls of the vena cava or other vessel, and may, for example, take the form of roughened portions of the wires. Preferably, the anchoring elements 7 are formed as small barbs having generally proximally oriented sharp ends. The barbs 7 may be fashioned from the end portions of hypodermic needles having an interior diameter closely receiving the wires, the barbs being crimped, welded, or otherwise fastened to the distal portions of anchoring wires 6 to hold them in place. To prevent the ends of the wires from penetrating the walls of the vena cava or other vessel, the wires may terminate distally in enlarged, bulbous or sphere-shaped ends which can be formed by known manufacturing procedures.

Figure 1A:
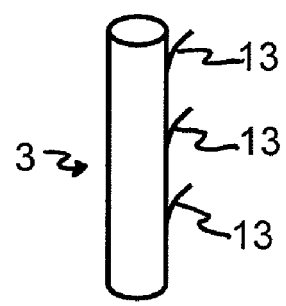
FIG. 1A is a side view of an enlargement of connecting tube 3 shown with connecting tube anchoring elements 13.

The assembly of the cores 5 is shown as being generally cylindrical in shape. The wires may be affixed to the core by crimping, chemically through the use of adhesives, thermally as by welding, etc. The distal ends of the wires may be received within circumferentially spaced bores in the core body so that the wires protrude distally from the distal end of the core body and are further formed into the extraction appendage, such as a U-shaped shown in FIG. 1. as appendage 4. Alternatively, an extraction appendage may be included and attached to the core 5 as a feature independent of the wires. As required, the wires may be cemented, crimped, or otherwise fastened to the core to restrain any significant axial rotational movement of the wires in the core. Further and as known to those skilled in the art, axial movement of the wires relative to the cores may be prevented by subsequent heat treatment of the wires into their desired geometries. Although the assembly of wires in the core has been described in connection with the filter elements 2, it will be understood that the anchoring wire 6 is similarly assembled and mounted in at least one of the cores. As shown in FIG. 1A, the connecting tubes 3 may have fixation elements 13 which prevent further migration of the filter.

Figure 2:
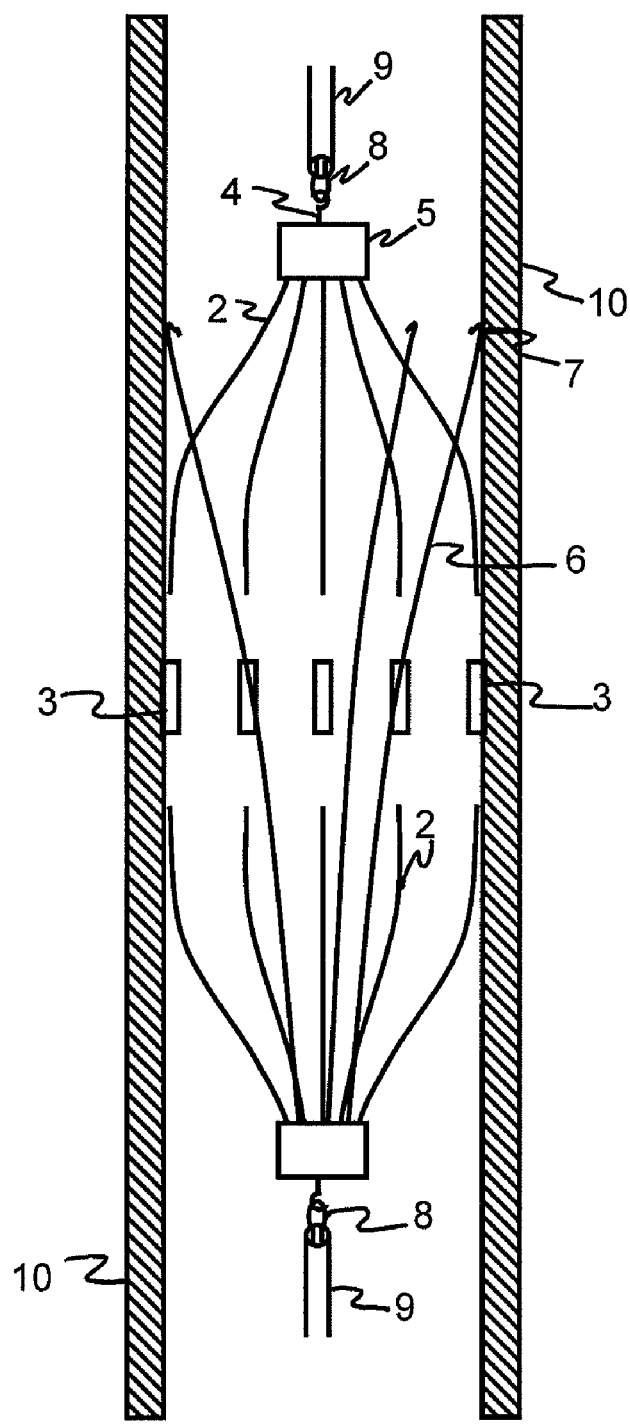
FIG. 2 is a side view of the filter being extracted from a vessel, where the vessel is shown in longitudinal cross section and the first and second portions have been separated.

Referring now to FIG. 2, which shows the filter assembly of the invention during extraction from a vessel, the vessel being shown in a cross sectional view, it can be seen that the first and second portions of the filter assembly have been disengaged from the connecting tubes 3 by application of a pulling force to the extraction appendage 4 where the force is applied in the direction opposite the distal ends of the filter wires 2 of the portion being pulled. The connecting tubes 3 are shown as partially integrated into the aortic wall 10, as occurs after deployment of the filter assembly for a period of time. As can be seen in general from FIG. 2, the filter wires 2 are extracted from the connecting tubes 3 such that the filter wires do not substantially disrupt the aortic wall, as they have been sequestered from the wall by the connecting tubes which are safely left behind after extraction of the first and second portions of the filter assembly.

Figure 3A:
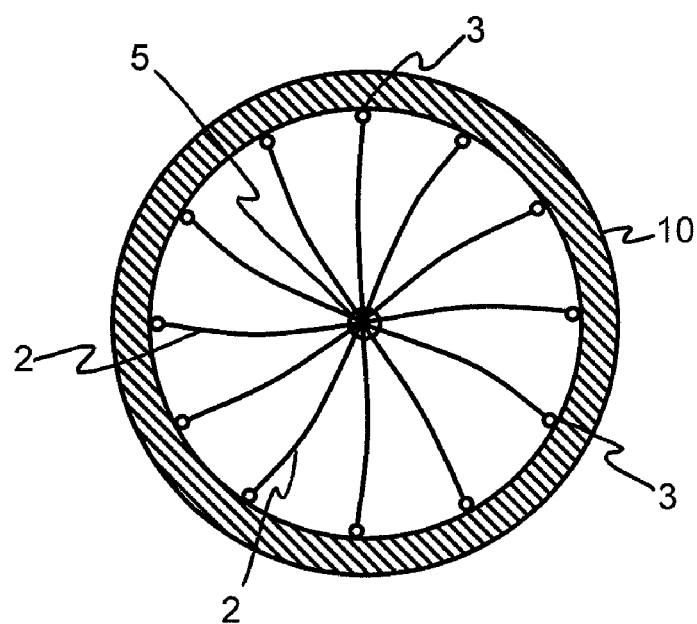
FIG. 3A is a cross sectional view of the filter shortly after insertion into a vessel.
Figure 3B:
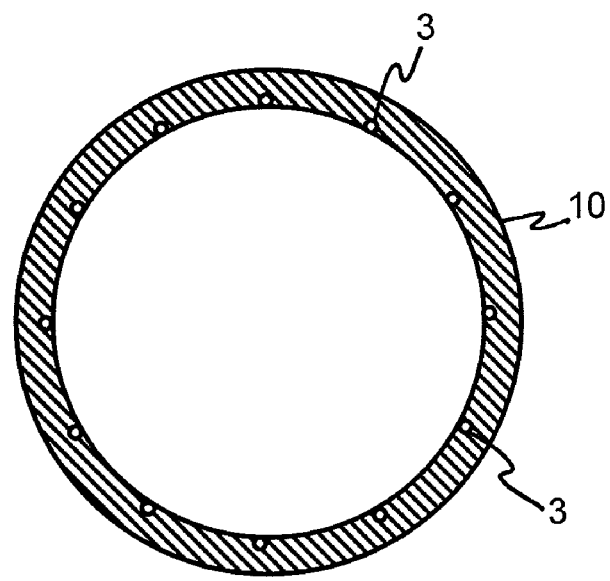
FIG. 3B is a cross sectional view of the vessel after extraction of the filter portions with the incorporated connecting tube segments left behind.

Referring now to FIG. 3A, a cross sectional view of the filter assembly shortly after deployment into a vessel is shown. The cross sectional view is drawn through the connecting tubes 3. As can be seen, the connecting tubes 3 are in contact with, but have not integrated into the vessel wall 10. In contrast, FIG. 3B. is a cross sectional view of the vessel post-retrieval of the filter assembly after the filter assembly has been deployed for a period of time sufficient to allow integration of the connecting tubes into the aortic wall. As can be seen, the connecting tubes 3 are integrated in the vessel wall and are safely left behind. Those skilled in the art will recognize that the filter assembly may be extracted at any time from immediately following deployment to complete integration of the connecting tubes within the aortic wall. Further, the filter assembly may be left in place indefinitely in a manner similar to conventional filters.

Figure 4:
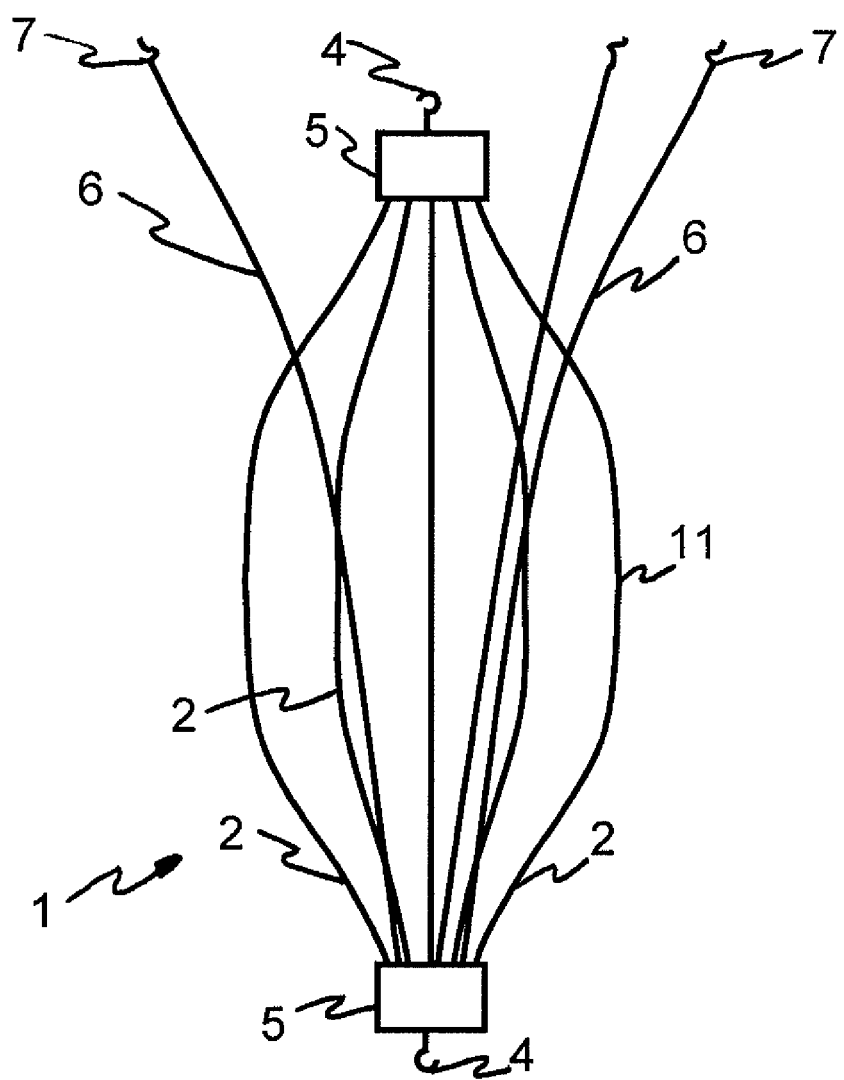
FIG. 4 is a side view of an embodiment of the filter assembly which is not separable into portions.

Another embodiment is shown in FIG. 4. This configuration of the filter is similar to the embodiments described above with the exception that the filter assembly is not separable into portions. Rather than connecting tubes, the filter wires 11 are singular wires that are each fixed to each core 5 by a fixation method as described above. Further, the filter wires 11 are sharpened such that they each comprise at least one sharp edge facing the center of the filter such that simultaneous application of a pulling force on the extraction appendages 4 in opposite directions, or application of a pulling force on either extraction appendage 4, allows the filter wires 11 to slice through the portion of the aortic wall between the wires and the longitudinal axis of the filter. Once the filter wires 11 are free from the aortic wall the filter can be collapsed into a removal catheter as described above or using other well known methods.

While preferred embodiments of the present invention have been described, it should be understood that various changes, adaptations and modifications may be made therein without departing from the spirit of the invention and the scope of the appended claims. Accordingly, the above disclosure generally describes the present invention. However, methods of cardiology and vascular surgery used but not explicitly described in this disclosure are amply reported in the scientific literature and are well within the ability of those skilled in the art.

I claim:

1. A catheter-deliverable and catheter-extractable filter assembly comprising:
a first portion and a second portion disposed along a longitudinal axis and each having a proximal and a distal end, wherein each of the first and second portions have a core from which extend a plurality of circumferentially spaced filter wires extending radially outwardly and axially in the direction of the opposite core, each core further comprising an extraction appendage, wherein at least one of the first or second portions of the filter assembly further comprises at least one anchoring wire extending from the core, wherein said at least one anchoring wire further comprises at least one anchoring element, and wherein the first and second portions are detachably connected by insertion of the distal ends of the filter wires into connector tubes such that the connector tubes are configured to remain in a vessel after extraction of the first and second portions.

2. The filter assembly of claim 1, wherein the connector tubes are distributed in a plane perpendicular to the longitudinal axis of the filter assembly.

3. The filter assembly of claim 1, wherein the connector tubes are distributed in a staggered configuration relative to the longitudinal axis of the filter assembly.

4. The filter assembly of claim 1, wherein the at least one anchoring element is spheroid.

5. The filter assembly of claim 1, wherein the at least one anchoring element is a barb.

6. The filter assembly of claim 1, wherein the extraction appendage is a loop.

7. The filter assembly of claim 1, wherein the extraction appendage is a hook.

8. The filter assembly of claim 1, wherein the connector tubes comprise an anchoring element.

* * * * *